(12) United States Patent
Ueda et al.

(10) Patent No.: US 11,116,957 B2
(45) Date of Patent: Sep. 14, 2021

(54) MEDICAL CONNECTOR

(71) Applicant: TERUMO KABUSHIKI KAISHA, Tokyo (JP)

(72) Inventors: Yasuhiro Ueda, Kofu (JP); Takeshi Toyama, Yamanashi (JP)

(73) Assignee: TERUMO KABUSHTKT KAISHA, Tokyo (JP)

( * ) Notice: Subject to any disclaimer, the term of this patent is extended or adjusted under 35 U.S.C. 154(b) by 178 days.

(21) Appl. No.: 15/717,353

(22) Filed: Sep. 27, 2017

(65) Prior Publication Data

US 2018/0015278 A1 Jan. 18, 2018

Related U.S. Application Data

(63) Continuation of application No. PCT/JP2016/001646, filed on Mar. 22, 2016.

(30) Foreign Application Priority Data

Mar. 27, 2015 (JP) .............................. JP2015-065800

(51) Int. Cl.
*A61M 39/00* (2006.01)
*A61M 39/26* (2006.01)
(Continued)

(52) U.S. Cl.
CPC ............. *A61M 39/26* (2013.01); *A61M 39/10* (2013.01); *A61M 2039/224* (2013.01); *A61M 2039/261* (2013.01)

(58) Field of Classification Search
CPC ......................... A61M 2039/224; A61M 39/26
See application file for complete search history.

(56) References Cited

U.S. PATENT DOCUMENTS 4,915,687 A * 4/1990 Sivert .................... A61M 39/02
137/605
5,163,922 A * 11/1992 McElveen, Jr. ........ A61M 39/02
251/149.1
(Continued)

FOREIGN PATENT DOCUMENTS

JP H10-323397 A 12/1998
JP 2001-170188 A 6/2001
(Continued)

OTHER PUBLICATIONS

International Search Report issued in International Patent Application No. PCT/JP2016/001646, dated May 24, 2016.
(Continued)

*Primary Examiner* — William R Carpenter
(74) *Attorney, Agent, or Firm* — Foley & Lardner LLP

(57) ABSTRACT

A medical connector includes a medical device connection portion communication passage defined by a housing and a valve body to guide a fluid from a first medical device connection portion to a second medical device connection portion. In the medical connector, a male connector inserted into the a connector connection portion presses a head portion of the valve body while contracting and deforming a body portion, and a fluid is guided from the male connector connection portion to the medical device connection portion communication passage, through a gap formed between the head portion and the housing.

15 Claims, 15 Drawing Sheets

(51) Int. Cl.
*A61M 39/10* (2006.01)
*A61M 39/22* (2006.01)

(56) References Cited

U.S. PATENT DOCUMENTS

| | | | | |
|---|---|---|---|---|
| 5,573,516 | A * | 11/1996 | Tyner | A61M 39/26 |
| | | | | 137/843 |
| 6,228,069 | B1 * | 5/2001 | Barth | A61M 39/26 |
| | | | | 604/249 |
| 6,569,117 | B1 | 5/2003 | Ziv et al. | |
| 7,837,658 | B2 * | 11/2010 | Cote, Sr. | A61M 39/045 |
| | | | | 604/236 |
| 9,067,049 | B2 * | 6/2015 | Panian | A61M 39/22 |
| 10,322,274 | B2 * | 6/2019 | Ueda | A61M 39/20 |
| 10,688,293 | B2 * | 6/2020 | Ueda | A61M 39/26 |
| 2004/0195538 | A1 * | 10/2004 | Raines | A61M 39/26 |
| | | | | 251/149.4 |
| 2006/0163515 | A1 * | 7/2006 | Ruschke | A61M 39/26 |
| | | | | 251/149.7 |
| 2006/0293629 | A1 * | 12/2006 | Cote, Sr. | A61M 39/045 |
| | | | | 604/246 |
| 2014/0332091 | A1 * | 11/2014 | Ueda | A61M 39/26 |
| | | | | 137/15.18 |
| 2016/0144110 | A1 * | 5/2016 | Ueda | A61M 39/223 |
| | | | | 604/256 |
| 2017/0007819 | A1 * | 1/2017 | Ueda | A61M 39/10 |
| 2017/0014618 | A1 * | 1/2017 | Ueda | A61M 39/1011 |
| 2018/0015278 | A1 * | 1/2018 | Ueda | A61M 39/10 |

FOREIGN PATENT DOCUMENTS

| | | | | |
|---|---|---|---|---|
| JP | 2001170188 A * | 6/2001 | | A61M 39/26 |
| JP | 2006-515220 A | 5/2006 | | |
| JP | 2008-540045 A | 11/2008 | | |
| JP | 2012-024565 A | 2/2012 | | |
| JP | 2013-500453 A | 1/2013 | | |
| WO | WO-0143814 A1 * | 6/2001 | | A61M 39/26 |
| WO | WO-2009/144599 A1 | 12/2009 | | |
| WO | WO-2015/145998 A1 | 10/2015 | | |

OTHER PUBLICATIONS

Office Action dated May 19, 2020 in corresponding Japanese Patent Application No. 2017-509260.

* cited by examiner

MEDICAL CONNECTOR

CROSS-REFERENCE TO RELATED APPLICATIONS

The present application is a bypass continuation of PCT/JP2016/001646, filed on Mar. 22, 2016, which claims priority to Japanese Application No. 2015-065800, filed on Mar. 27, 2015. The contents of these applications are hereby incorporated by reference in their entireties.

BACKGROUND

The present application relates to a medical connector including a housing having a first medical device connection portion, a second medical device connection portion, and a male connector connection portion, and a valve body having a head portion capable of closing the male connector connection portion, and a body portion extending from the head portion, more particularly, to a medical connector inhibiting generation of drawing of a fluid in a second medical device connection portion upon removal of a male connector from the male connector connection portion, and inhibiting generation of stagnation of a fluid in the medical connector.

BACKGROUND ART

A medical connector may be used for various medical devices, infusion containers, liquid delivery devices, or the like, to connect a tube body of a medical device. For example, a medical connector described in JP H10-323397 A and JP 2013-500453 A includes a housing having a first medical device connection portion, a second medical device connection portion, and a male connector connection portion, a valve body having a head portion capable of closing the male connector connection portion, and a body portion extending from the head portion, and a medical device connection portion communication passage defined by the housing and the valve body and guiding a fluid from the first medical device connection portion to the second medical device connection portion.

In a medical connector illustrated in FIGS. 1 to 3 of JP H10-323397 A, a branch is connected to a medical device connection portion communication passage, and the branch includes a hollow portion having an end portion closed by the head portion of the valve body, and penetrating the body portion of the valve body. Then, a male connector inserted into a male connector connection portion presses the head portion of the valve body to open a slit bored in the head portion, and a fluid is guided from a male connector connection portion to the medical device connection portion communication passage, through the slit and the hollow portion.

Furthermore, in a medical connector illustrated in FIG. 38 of JP 2013-500453 A, a male connector inserted into a male connector connection portion presses a head portion of a valve body while contracting and deforming a body portion, and a fluid is guided from the male connector connection portion to an upstream side of a medical device connection portion communication passage, through a gap formed between the head portion and a housing. Furthermore, this medical connector is provided with an additional flow passage between the body portion of the valve body and the housing, and the fluid is guided from the male connector connection portion to a downstream side of the medical device connection portion communication passage, through the gap formed upon insertion of the male connector, and the additional flow passage.

SUMMARY

However, as described in JP H10-323397 A, the medical connector having a configuration to guide a fluid through the hollow portion penetrating the body portion of the valve body disadvantageously draws the fluid from the second medical device connection portion into the housing, upon removing the male connector from the male connector connection portion. When the fluid is drawn from the second medical device connection portion into the housing upon removal of the male connector, for example, use of the medical connector connected to a catheter placed in a blood vessel may cause the following problems.

That is, when the male connector is removed, after the male connector is inserted into the male connector connection portion of the medical connector and an anticoagulant agent is injected through the male connector, the fluid-drawing from the second medical device connection portion to which the catheter is connected, causes blood-drawing into the catheter, blood is coagulated in the catheter, and the catheter is clogged and cannot be used.

Furthermore, as described in JP H10-323397 A, in a medical connector having a configuration to guide a fluid through the branch upon insertion of the male connector to the male connector connection portion, when the male connector is not inserted, the fluid flowing in the medical device connection portion communication passage does not flow in the branch, the fluid stagnates in the branch, and contamination, such as growth of unwanted bacteria, may be caused in the stagnation portion.

Furthermore, as described in JP 2013-500453 A, in a medical connector having a configuration including the additional flow passage between the body portion of the valve body and the housing to guide a fluid from the male connector connection portion to the medical device connection portion communication passage through the gap formed upon insertion of the male connector and the additional flow passage, when the male connector is not inserted, the fluid flowing in the medical device connection portion communication passage does not flow in the additional flow passage, the fluid stagnates in the flow passage, and contamination may be caused in the stagnation portion.

Embodiments described in this application have been developed in view of the above findings, and an object of certain embodiments is to provide a medical connector inhibiting generation of drawing of a fluid in a second medical device connection portion upon removal of a male connector from a male connector connection portion, and inhibiting generation of stagnation of a fluid in the medical connector.

In one embodiment, a medical connector includes a housing having a first medical device connection portion, a second medical device connection portion, and a male connector connection portion, a valve body having a head portion capable of closing the male connector connection portion, and a body portion extending from the head portion, and a medical device connection portion communication passage defined by the housing and the valve body to guide a fluid from the first medical device connection portion to the second medical device connection portion, and in the medical connector, a male connector inserted into the male connector connection portion presses the head portion of the valve body while contracting and deforming the body portion, and a fluid is guided from the male connector connection portion to the medical device connection portion communication passage, through only a gap formed between the head portion and the housing.

In one aspect, the body portion forms an inner space therein so that, when the body portion is contracted and deformed, the inner space is liquid-tightly divided from a fluid flowing in the medical device connection portion communication passage.

In one aspect, the housing includes a recessed storage portion for storing the body portion of the valve body, the valve body is provided with a circumferential sealing portion making sliding contact with the recessed storage portion, on an outer peripheral surface of the body portion, and the outer peripheral surface of the body portion has a region opposite to the head portion across the sealing portion and liquid-tightly divided from a fluid flowing in the medical device connection portion communication passage.

In one aspect, while the male connector is not inserted, a region of at least ½ of the outer peripheral surface of the valve body makes contact with the housing, or is liquid-tightly divided from a fluid flowing in the medical device connection portion communication passage.

In one aspect, while the male connector is not inserted, a region of at least ½ of the outer peripheral surface of the valve body is in contact with the housing.

In one aspect, the medical device connection portion communication passage preferably includes an annular flow passage surrounding an outer peripheral surface of the body portion of the valve body.

According to certain embodiments described in this application, the male connector inserted into the male connector connection portion presses the head portion of the valve body while contracting and deforming the body portion, and a fluid can be guided from the male connector connection portion to the medical device connection portion communication passage, through only the gap formed between the head portion and the housing. Then, when the male connector is removed from the male connector connection portion, the body portion of the valve body expands and deforms for restoration, and the gap is closed.

Therefore, according to certain embodiments, an increase in fluid flow passage volume in the housing, which may occur in removing the male connector, can be inhibited using an amount of expansion of the body portion of the valve body upon restoration of the body portion, and thus, generation of drawing of a fluid in the second medical device connection portion can be inhibited upon removal of the male connector. Furthermore, according to certain embodiments, because a fluid is guided from the male connector connection portion to the medical device connection portion communication passage, through only the gap formed between the head portion and the housing upon insertion of the male connector, formation of a stagnation portion, in which the fluid flowing in the medical device connection portion communication passage stagnates, is inhibited while the male connector is not inserted.

Accordingly, in certain embodiments, a medical connector can be provided which inhibits generation of drawing of a fluid in a second medical device connection portion upon removal of a male connector from a male connector connection portion, and inhibits generation of stagnation of a fluid in the medical connector.

DETAILED DESCRIPTION

Hereinafter, embodiments of the medical connector will be described in detail with reference to FIGS. 1 to 12.

Figure 1:
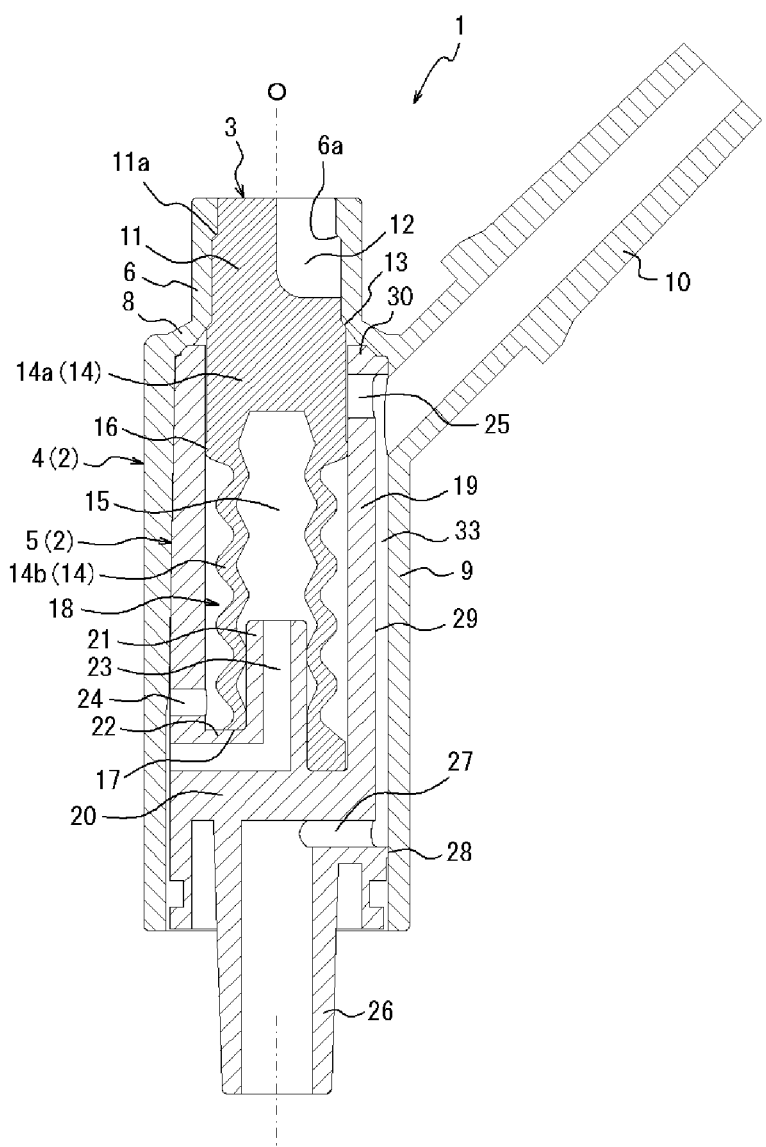
FIG. 1 is a vertical cross-sectional view of a medical connector according to an embodiment of the present invention, where the male connector is not inserted.

In the present description, "vertically" represents a direction along a center axis of a male connector connection portion of the medical connector, "upward" represents a direction in which a male connector is removed (i.e., upward in FIG. 1), and "downward" represents a direction in which a male connector is inserted (i.e., downward in FIG. 1).

Figure 2:
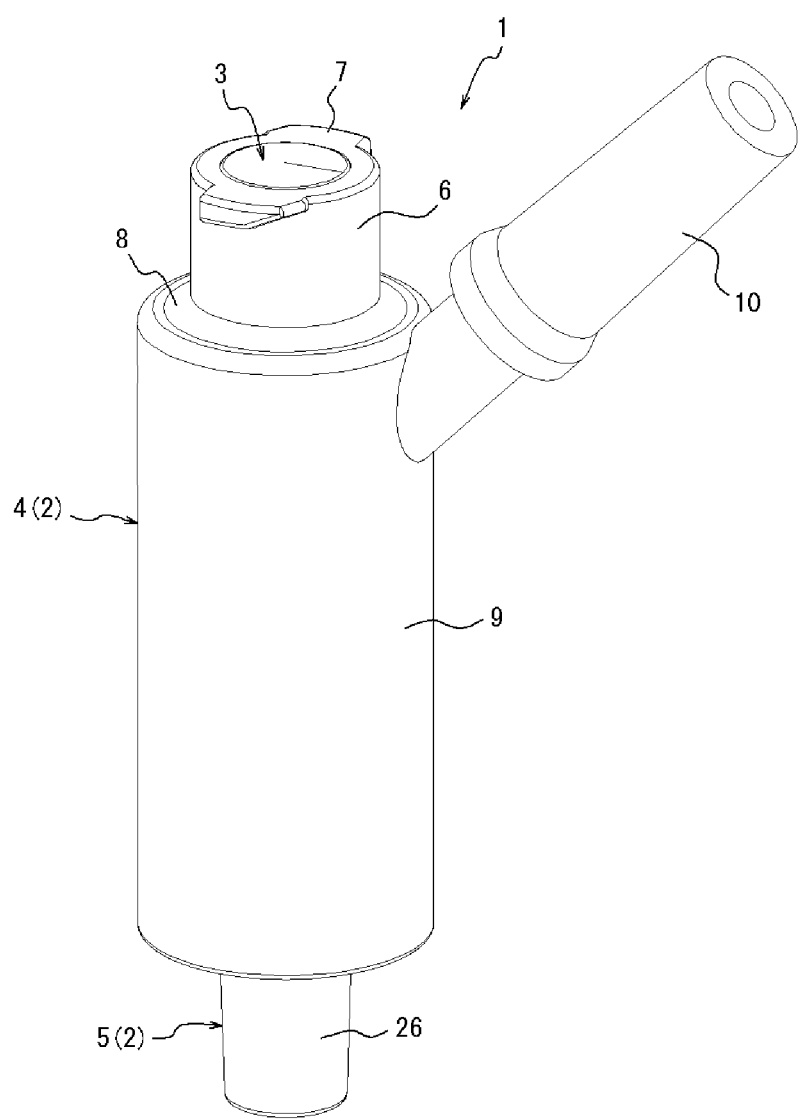
FIG. 2 is a perspective view of the medical connector illustrated in FIG. 1.
Figure 3:
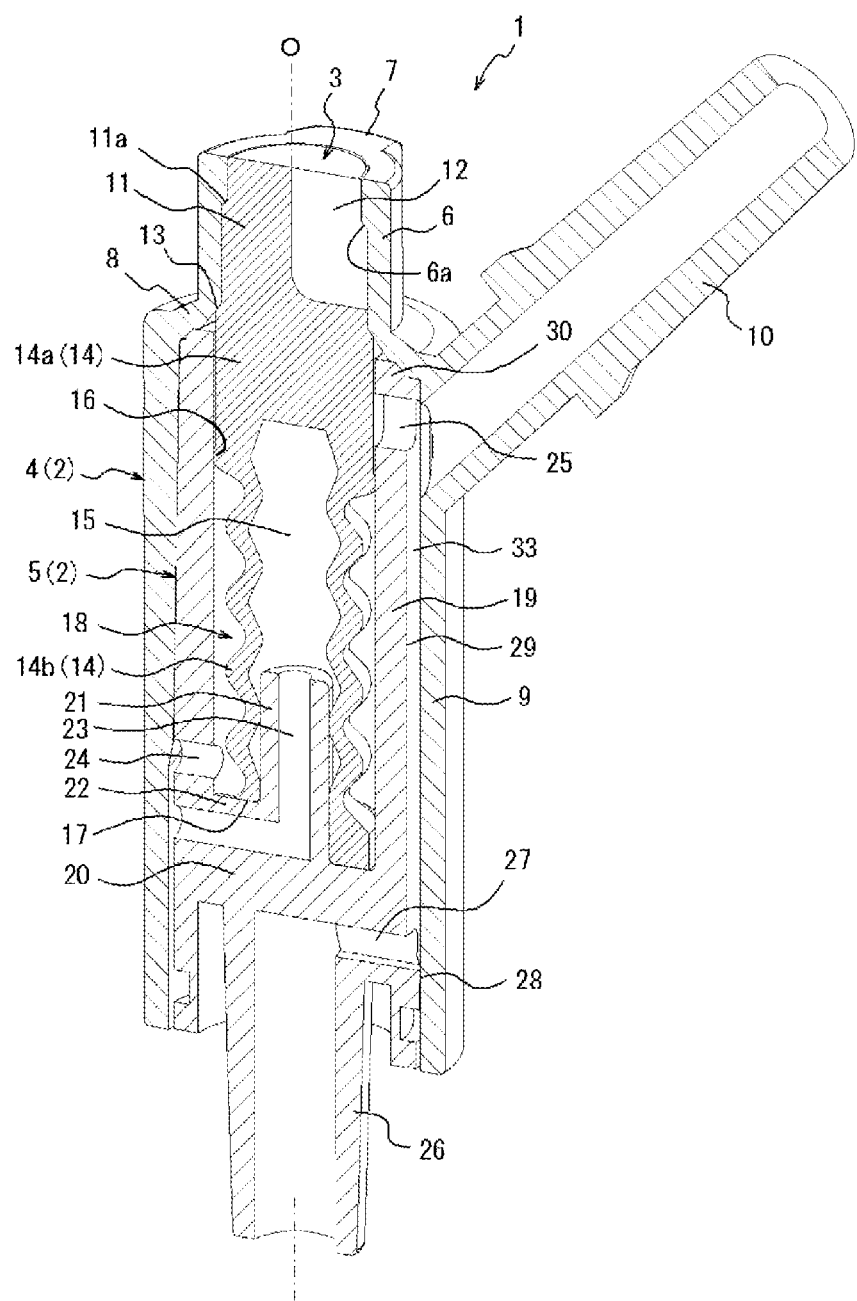
FIG. 3 is a perspective vertical cross-sectional view of the medical connector illustrated in FIG. 1.
Figure 4:
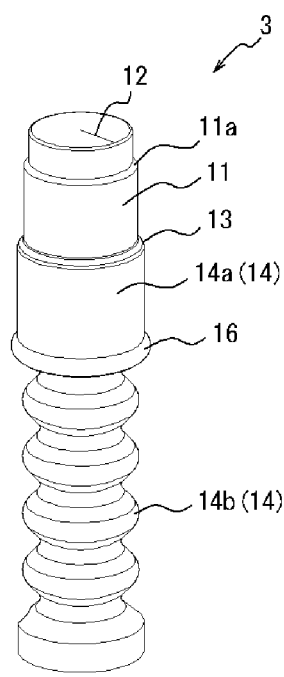
FIG. 4 is a perspective view of a valve body of the medical connector illustrated in FIG. 1.
Figure 5:
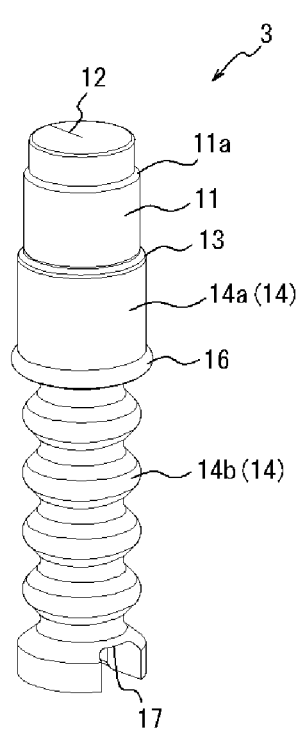
FIG. 5 is a perspective view of the valve body illustrated in FIG. 4, as viewed from another angle.
Figure 6:
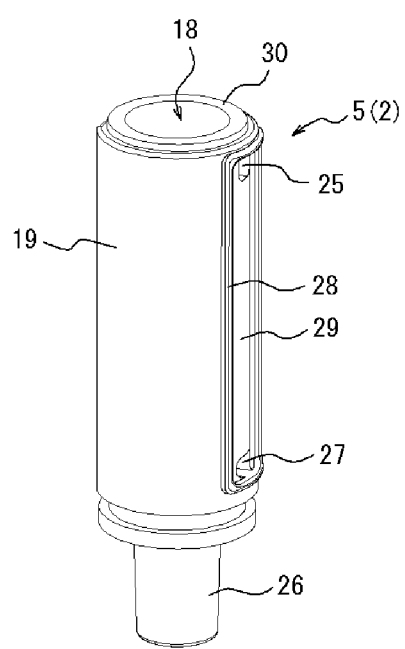
FIG. 6 is a perspective view of an inner housing of the medical connector illustrated in FIG. 1.

As illustrated in FIGS. 1 to 3, a medical connector 1 includes a housing 2 and a valve body 3. In the present embodiment, the housing 2 includes an outer housing 4 and an inner housing 5, and the outer housing 4 is fixed to the inner housing 5. The outer housing 4 and the inner housing 5 are secured to each other by, for example, welding or bonding. Furthermore, when the outer housing 4 and the inner housing 5 are made of a synthetic resin, for example, heat welding may be employed to secure the housings. In the present example, the housing 2 is constituted by two members of the outer housing 4 and the inner housing 5, but instead of this, the housing may be constituted by, for example, one or three members according to a manufacturing method to be employed. As a material of the valve body 3, for example, a rubber material or a thermoplastic elastomer is preferably used.

The outer housing 4 has an upper end provided with a male connector connection portion 6 having a cylindrical shape about an axis O. In the present example, the male connector connection portion 6 has an outer peripheral surface on which a locking projection 7 for securing a luer lock male connector is formed at an upper end. The locking projection 7 can be omitted. The male connector connection portion 6 has a lower end at which an outer peripheral wall portion 9 having a cylindrical shape is provided to hang down through a tapered wall portion 8 tapered with increasing diameter. The outer peripheral wall portion 9 has an upper end provided with a first medical device connection portion 10 projecting obliquely upward.

As illustrated in FIGS. 1 to 5, the valve body 3 includes a head portion 11 having a columnar shape about the axis O. In the present example, the male connector connection portion 6 has an inner peripheral surface provided with an annular stepped portion 6a increasing in diameter downward, and the head portion 11 of the valve body 3 is provided with an annular stepped portion 11a closely fitted to the annular stepped portion 6a. In the head portion 11, a slit 12 is formed to linearly extend in a radial direction from a center axis O. The head portion 11 has a lower end from which a body portion 14 is extended through a shoulder portion 13 tapered with increasing diameter at an angle the same as inclination of an inner peripheral surface of the tapered wall portion 8 of the outer housing 4.

The body portion 14 has an upper portion 14a formed to have a columnar shape about the axis O, and a vertically intermediate portion and a lower portion formed as a bellows portion 14b. Furthermore, a hollow portion 15 as an inner space is formed in the body portion 14. Specifically, the hollow portion 15 opening at an end opposite to the head portion 11 is formed in the body portion 14. The bellows portion 14b has an outer peripheral surface provided at an upper end with a circumferential sealing projection 16 (see FIGS. 4 and 5) as a sealing portion making sliding contact with a recessed storage portion 18 described later. The bellows portion 14b has a lower end provided with a recessed portion 17 engaged with a protruding portion 22 formed in the recessed storage portion 18 described later to inhibit circumferential rotation of the body portion 14. The hollow portion 15 configured as the inner space is liquid-tightly divided from a fluid flowing in a medical device connection portion communication passage 33 described later, when the body portion 14 is contracted and deformed.

As illustrated in FIGS. 1, 3, and 6 to 8, the recessed storage portion 18 in which the body portion 14 of the valve body 3 is disposed is formed in the inner housing 5. The recessed storage portion 18 is defined by an inner peripheral surface of an inner peripheral wall portion 19 having a cylindrical shape about the axis O, and an upper surface of a bottom wall portion 20 extending from a lower end of the inner peripheral wall portion 19. The upper surface of the bottom wall portion 20 has an insertion projection 21 formed at the center to project upward to be inserted into the hollow portion 15 of the valve body 3. Furthermore, the protruding portion 22 engaged with the recessed portion 17 of the valve body 3 described above to inhibit circumferential rotation of the body portion 14 is formed on the upper surface of the bottom wall portion 20.

A first air passage 23 for connecting the hollow portion 15 of the valve body 3 to an outer peripheral space of the inner peripheral wall portion 19 is formed in the insertion projection 21 and the protruding portion 22. Furthermore, a second air passage 24 for connecting a space defined by the recessed storage portion 18 and the outer peripheral surface of the bellows portion 14b of the valve body 3 to the outer peripheral space of the inner peripheral wall portion 19 is formed in the inner peripheral wall portion 19. The first air passage 23 and the second air passage 24 each communicate with an outer space of the medical connector 1 through a gap between the inner peripheral wall portion 19 and the outer peripheral wall portion 9 of the outer housing 4.

The inner peripheral wall portion 19 includes a first through-hole 25 at a position facing a flow passage in the first medical device connection portion 10. Furthermore, the bottom wall portion 20 has a lower portion in which a second medical device connection portion 26 is formed. A second through-hole 27 for connecting a flow passage in the second medical device connection portion 26 to the outer peripheral space of the inner peripheral wall portion 19 is formed in the lower end of the inner peripheral wall portion 19. Both of the first through-hole 25 and the second through-hole 27 are surrounded by a sealing projection 28 having substantially a rectangular shape (see FIG. 6). The sealing projection 28 has an inside formed as a recessed groove portion 29 recessed deeper than an outside of the sealing projection 28. Furthermore, the inner peripheral wall portion 19 has an upper edge circumferentially provided with a sealing projection 30 having an annular shape. The sealing projections 28 and 30 may be configured as separated members including an elastic material such as rubber or thermoplastic elastomer to be bonded to the inner peripheral wall portion 19, or may be formed integrally with the inner peripheral wall portion 19 of synthetic resin by insert-molding or the like.

Figure 7:
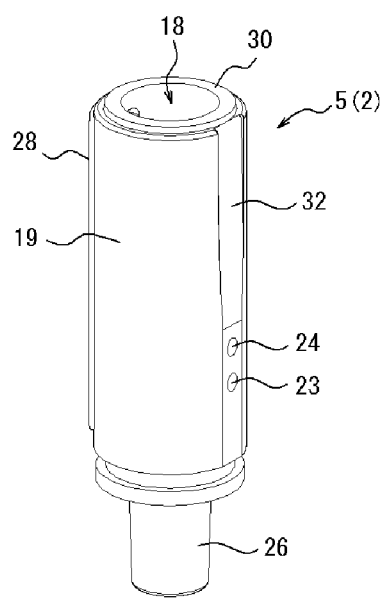
FIG. 7 is a perspective view of the inner housing illustrated in FIG. 6, as viewed from another angle.
Figure 8:
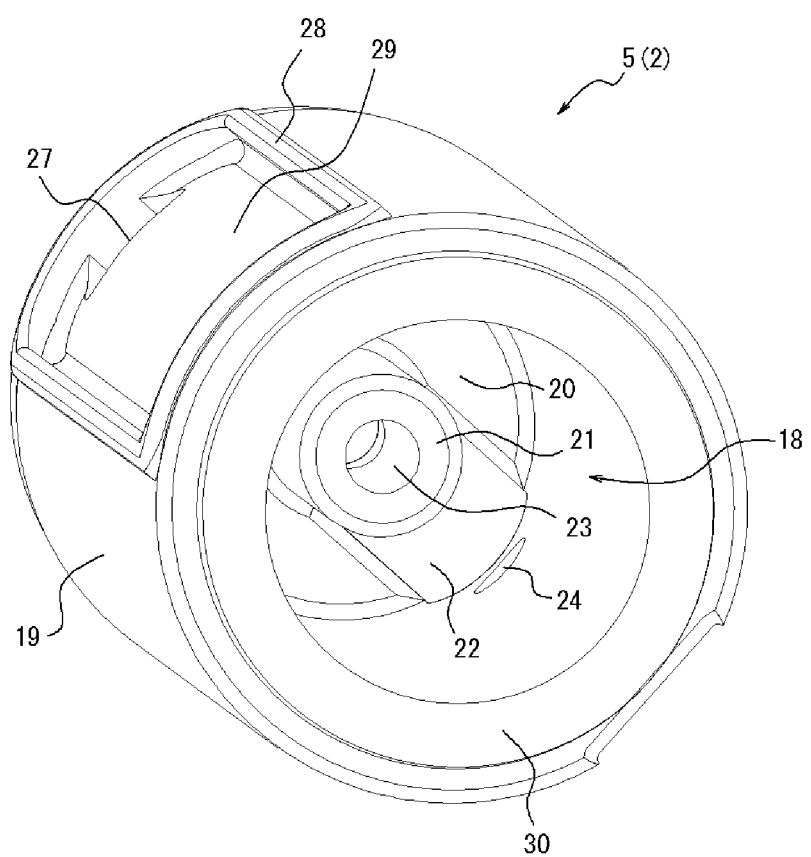
FIG. 8 is a perspective view of the inner housing illustrated in FIG. 6, as viewed from still another angle.
Figure 9:
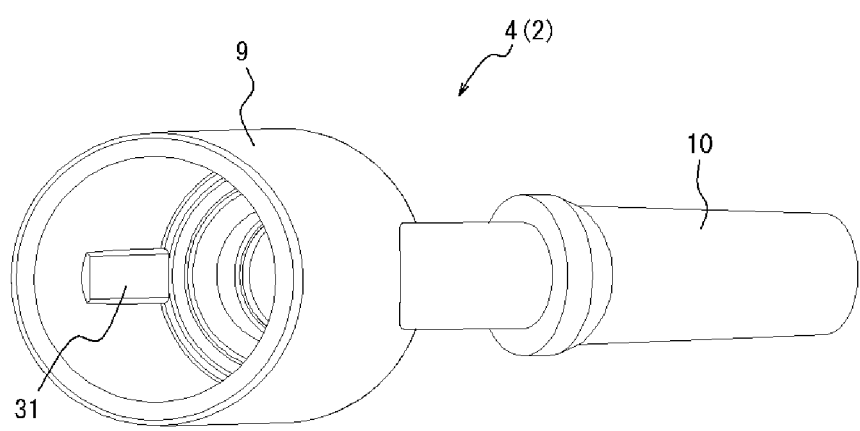
FIG. 9 is a perspective view of an outer housing of the medical connector illustrated in FIG. 1.

In the present example, as illustrated in FIG. 9, the outer peripheral wall portion 9 of the outer housing 4 has an inner peripheral surface provided with a positioning projection 31, and the positioning projection 31 is engaged with a positioning recessed portion 32 illustrated in FIG. 7.

As described above, the medical connector 1 according to the present embodiment includes the housing 2 having the first medical device connection portion 10, the second medical device connection portion 26, and the male connector connection portion 6, and the valve body 3 having the head portion 11 capable of closing the male connector connection portion 6, and the body portion 14 extending from the head portion 11. Furthermore, the medical connector 1 includes the medical device connection portion communication passage 33 defined by the housing 2 and the valve body 3, and guiding a fluid from the first medical device connection portion 10 to the second medical device connection portion 26. In the present example, the medical device connection portion communication passage 33 is defined by the body portion 14 of the valve body 3, the first through-hole 25, the recessed groove portion 29, the outer peripheral wall portion 9, and the second through-hole 27.

Figure 10:
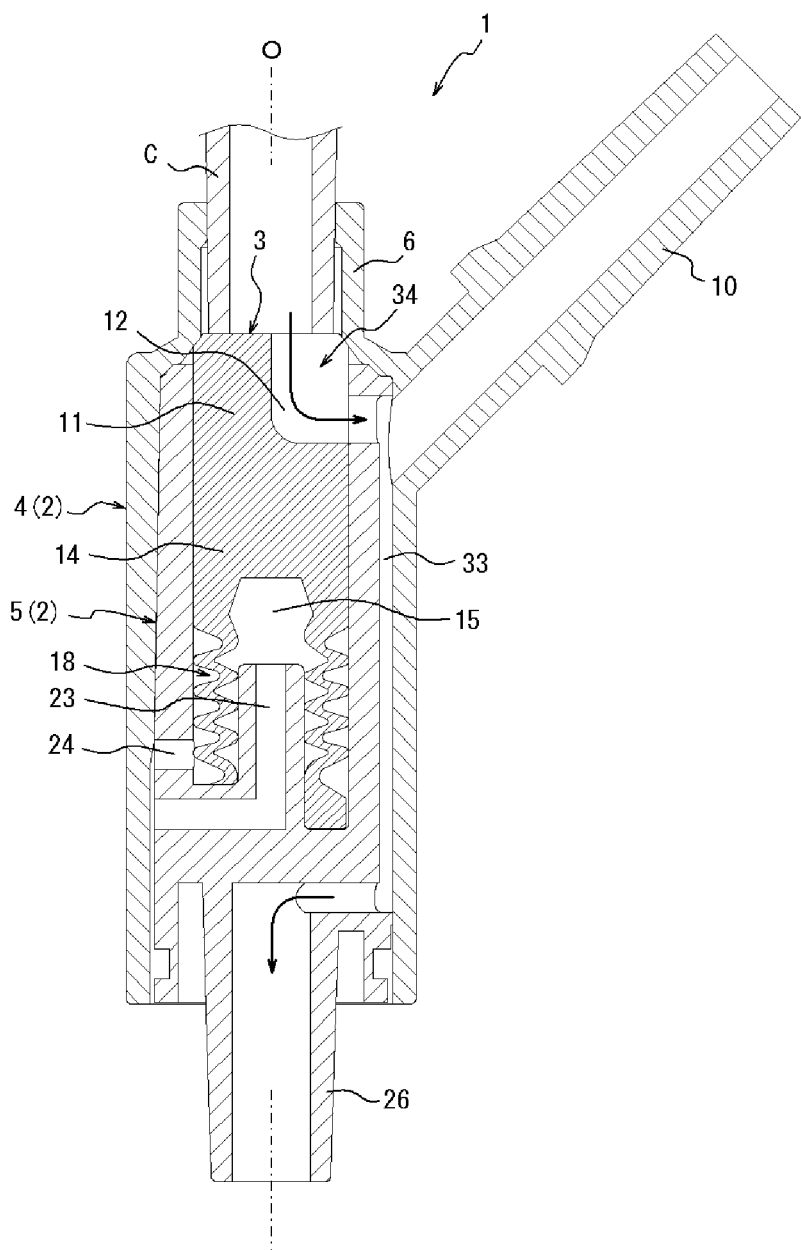
FIG. 10 is a vertical cross-sectional view of the medical connector illustrated in FIG. 1, where a male connector is inserted.

Furthermore, as illustrated in FIG. 10, the medical connector 1 is configured so that a male connector C inserted into the male connector connection portion 6 presses the head portion 11 of the valve body 3 while contracting and deforming the body portion 14 to guide a fluid from the male connector connection portion 6 to the medical device connection portion communication passage 33, through only a gap 34 formed between the head portion 11 and the housing 2. More specifically, in the present example, the gap 34 is defined by the slit 12 opened by pressing the head portion 11 of the valve body 3, and the housing 2. Then, when the male connector C is removed from the male connector connection portion 6, the body portion 14 of the valve body 3 expands and deforms for restoration, and the gap 34 is closed.

Therefore, according to the medical connector 1 increase in fluid flow passage volume in the housing 2, which may occur in removing the male connector C, can be inhibited using an amount of expansion of the body portion 14 of the valve body 3 upon restoration of the body portion 14, and thus, generation of drawing of a fluid in the second medical device connection portion 26 can be inhibited upon removal of the male connector C. Furthermore, according to the medical connector 1, since a fluid is guided from the male connector connection portion 6 to the medical device connection portion communication passage 33, through only the gap 34 formed between the head portion 11 and the housing 2 upon insertion of the male connector C, formation of a stagnation portion, in which the fluid flowing in the medical device connection portion communication passage 33 stagnates, is inhibited while the male connector C is not inserted.

Therefore, according to the medical connector 1, when the male connector C is removed from the male connector connection portion 6, generation of drawing of a fluid is inhibited in the second medical device connection portion 26, and generation of stagnation of the fluid is inhibited in the medical connector 1.

In the present embodiment, the medical connector 1 is configured so that the male connector C inserted into the male connector connection portion 6 presses the head portion 11 of the valve body 3 while contracting and deforming the body portion 14 to guide a fluid from the male connector connection portion 6 to the most upstream portion of the medical device connection portion communication passage 33, through only the gap 34 formed between the head portion 11 and the housing 2. Such a configuration can inhibit stagnation of a fluid flowing from the male connector C, in the medical device connection portion communication passage 33, while the male connector C is inserted.

Furthermore, in the present embodiment, the body portion 14 of the valve body 3 forms the inner space (hollow portion 15), and the inner space is liquid-tightly divided from a fluid flowing in the medical device connection portion communication passage 33 upon contraction and deformation of the body portion (see FIG. 10). More specifically, in the present embodiment, the inner space (hollow portion 15) is liquid-tightly divided from a fluid flowing in the medical device connection portion communication passage 33, by the sealing portion (the sealing projection 16, see FIGS. 4 and 5) making sliding contact with the recessed storage portion 18.

Therefore, according to the medical connector 1, upon insertion and removal of the male connector C into and from the male connector connection portion 6, contraction and deformation, and expansion and deformation of the body portion 14 of the valve body 3 is facilitated for smooth insertion and removal of the male connector C.

In the present embodiment, since the medical connector 1 includes the first air passage 23 and the second air passage 24, the male connector C can be inserted and removed more smoothly, but the first air passage 23 and the second air passage 24 are not necessarily provided.

Furthermore, in the present embodiment, the housing 2 includes the recessed storage portion 18 for storing the body portion 14 of the valve body 3, the valve body 3 is provided with the circumferential sealing portion (the sealing projection 16, see FIGS. 4 and 5) making sliding contact with the recessed storage portion 18, on the outer peripheral surface of the body portion 14, and the outer peripheral surface of the body portion 14 has a region opposite to the head portion 11 across the sealing portion (i.e., a region below the sealing projection 16), and the region is liquid-tightly divided from a fluid flowing in the medical device connection portion communication passage 33. Therefore, upon removal of the male connector C, generation of increase and decrease in fluid flow passage volume can be inhibited in the housing 2. Therefore, according to the medical connector 1, upon removal of the male connector C from the male connector connection portion 6, not only generation of drawing of a fluid in the second medical device connection portion 26, but also generation of extrusion of the fluid can be inhibited. That is, according to the medical connector 1, for example, it can be also inhibited that when a drug is administered to a patient, the drug having an amount equal to an amount of this extrusion is unexpectedly administered to the patient with removal of the male connector C.

Furthermore, in the present embodiment, while the male connector C is not inserted, a region of at least ½, more preferably at least ⅔, of the outer peripheral surface of the valve body 3 is in contact with the housing 2, or is liquid-tightly divided from a fluid flowing in the medical device connection portion communication passage 33. More specifically, in the present embodiment, the valve body 3 is configured so that while the male connector C is not inserted, outer peripheral surfaces of the head portion 11, the shoulder portion 13, and the sealing projection 16 are in contact with the housing 2, and the region below the sealing projection 16 in the outer peripheral surface of the body portion 14, is liquid-tightly divided from a fluid flowing in the medical device connection portion communication passage 33. Then, the total area of the outer peripheral surfaces of the head portion 11, the shoulder portion 13, and the sealing projection 16, and the region below the sealing projection 16 in the outer peripheral surface of the body portion 14 is at least ½, more preferably at least ⅔, of the whole area of the outer peripheral surface of the valve body 3.

Therefore, according to the medical connector 1, while the male connector C is not inserted, the valve body 3 can have a surface small enough to be in contact with a fluid flowing in the medical device connection portion communication passage 33, and thus, formation of the stagnation portion of the fluid is inhibited more accurately.

Figure 11:
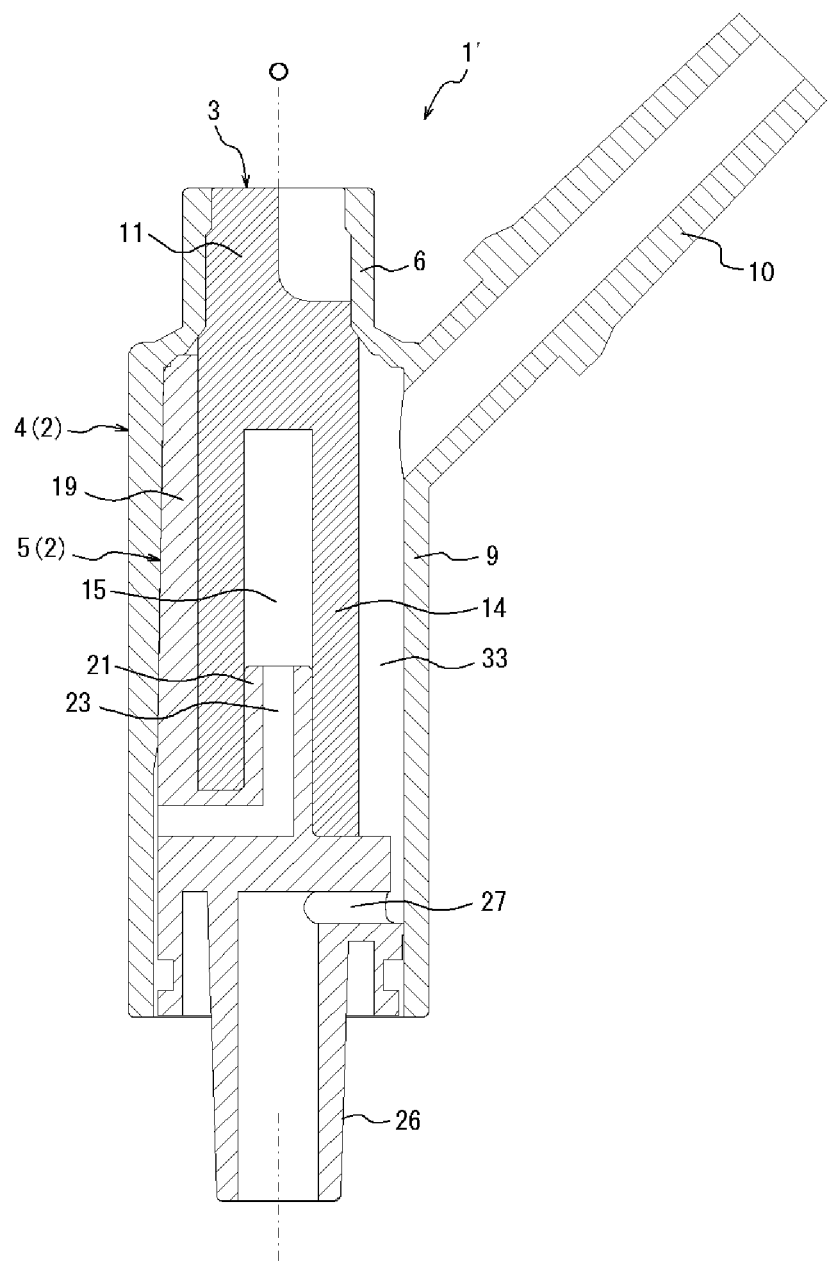
FIG. 11 is a vertical cross-sectional view illustrating a modification of the medical connector of FIG. 1.

Furthermore, the medical connector 1 according to the present embodiment is configured so that the housing 2 is provided with a recessed storage portion 18 for storing the body portion 14 of the valve body 3, but as a modification, the medical connector 1 may have a configuration without such a recessed storage portion 18, as illustrated in FIG. 11. That is, in the present modification, the inner peripheral wall portion 19 of the inner housing 5 is cut out, and the medical device connection portion communication passage 33 is defined by the cutout portion, the body portion 14 of the valve body 3, the outer peripheral wall portion 9, and the second through-hole 27.

Furthermore, in the present modification, the body portion 14 of the valve body 3 is preferably configured to have a columnar shape as illustrated in FIG. 11, and such a configuration inhibits formation of a stagnation portion of a fluid, between the inner peripheral wall portion 19 and the body portion 14 of the valve body 3. Furthermore, in the present modification, as illustrated in FIG. 11, the second air passage (see FIG. 1) provided in the above embodiment is not provided, and only the first air passage 23 can be provided. An outer peripheral edge of the cutout portion of the inner peripheral wall portion 19 and the upper edge of the inner peripheral wall portion 19 can be appropriately provided with sealing structures, such as the sealing projections 28 and 30 described above (see FIG. 6). The other configurations can be the same as those in the above embodiment.

Figure 12:
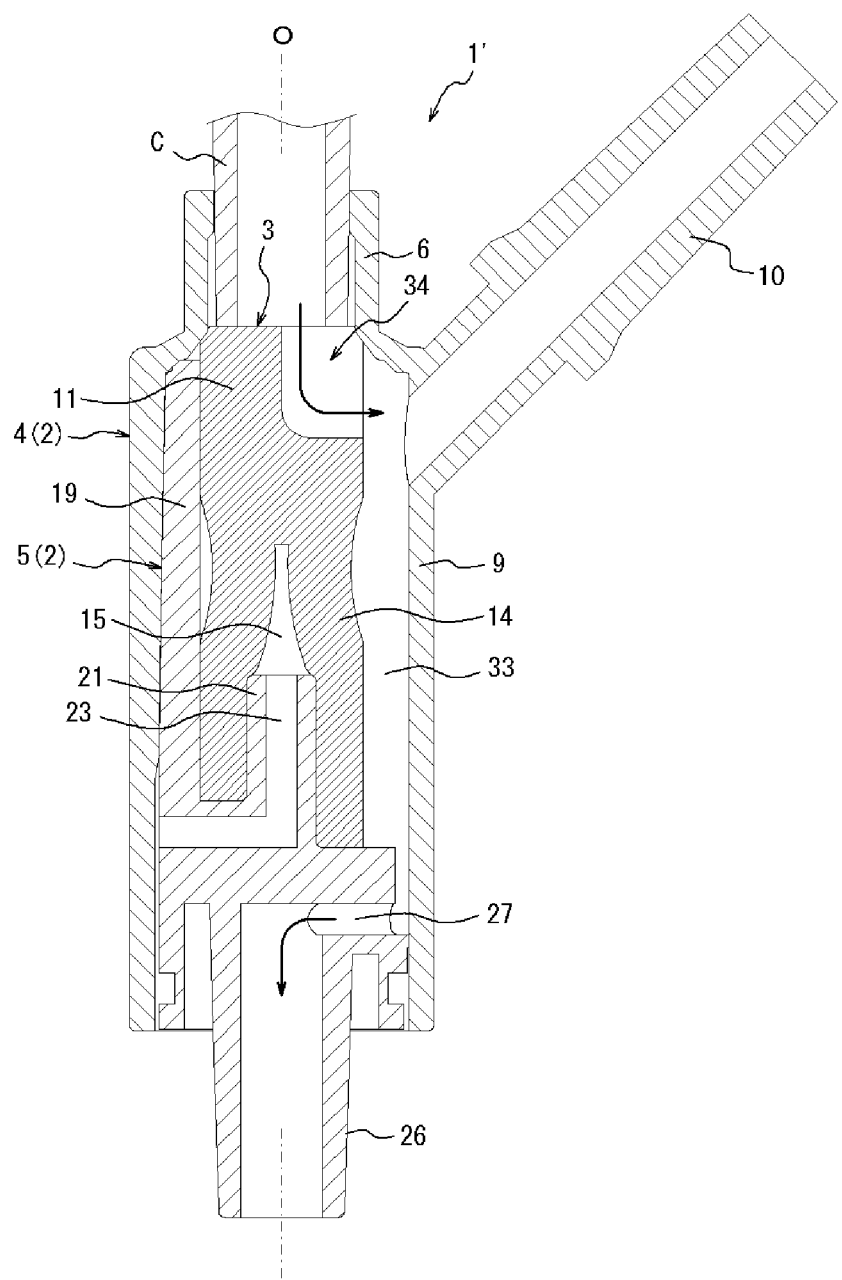
FIG. 12 is a vertical cross-sectional view of the medical connector illustrated in FIG. 11, where a male connector is inserted.

As illustrated in FIG. 12, in a medical connector 1' according to the present modification, having such a configuration, the male connector C inserted into the male connector connection portion 6 presses the head portion 11 of the valve body 3 while contracting and deforming the body portion 14 to guide a fluid from the male connector connection portion 6 to the medical device connection portion communication passage 33, through only the gap 34 formed between the head portion 11 and the housing 2, as in the above embodiment.

Therefore, according to the medical connector 1', increase in fluid flow passage volume in the housing 2, which may occur in removing the male connector C, can be inhibited using an amount of expansion of the body portion 14 of the valve body 3 upon restoration of the body portion 14, and thus, generation of drawing of a fluid in the second medical device connection portion 26 can be inhibited upon removal of the male connector C. Furthermore, according to the medical connector 1', since a fluid is guided from the male connector connection portion 6 to the medical device connection portion communication passage 33, through only the gap 34 formed between the head portion 11 and the housing 2 upon insertion of the male connector C, formation of the stagnation portion, in which the fluid flowing in the medical device connection portion communication passage 33 stagnates, is inhibited while the male connector C is not inserted.

In the present modification, the medical connector 1' is configured so that the male connector C inserted into the male connector connection portion 6 presses the head portion 11 of the valve body 3 while contracting and deforming the body portion 14 to guide a fluid from the male connector connection portion 6 to the most upstream portion of the medical device connection portion communication passage 33, through only the gap 34 formed between the head portion 11 and the housing 2, as in the above embodiment. Such a configuration can inhibit stagnation of a fluid flowing from the male connector C, in the medical device connection portion communication passage 33, while the male connector C is inserted.

Furthermore, in the present modification, the body portion 14 of the valve body 3 forms an inner space (hollow portion 15), and the inner space is liquid-tightly divided from a fluid flowing in the medical device connection portion communication passage 33 upon contraction and deformation of the body portion (see FIG. 12). More specifically, in the present embodiment, the inner space (hollow portion 15) is liquid-tightly divided from the fluid flowing in the medical device connection portion communication passage 33, by press-fitting the insertion projection 21 into the hollow portion 15.

Furthermore, in the present modification, while the male connector C is not inserted, a region of at least ½, more preferably at least ⅔, of the outer peripheral surface of the valve body 3 is in contact with the housing 2. More specifically, in the present modification, the valve body 3 is configured so that while the male connector C is not inserted, the outer peripheral surfaces of the head portion 11 and the shoulder portion 13, and part of the outer peripheral surface of the body portion 14 are in contact with the housing 2. Then, the total area of these portions in contact with the housing 2 is at least ½, more preferably at least ⅔, of the whole area of the outer peripheral surface of the valve body 3.

Therefore, according to the medical connector 1', while the male connector C is not inserted, the valve body 3 can have a surface small enough to be in contact with a fluid flowing in the medical device connection portion communication passage 33, and thus, formation of the stagnation portion of the fluid is inhibited more accurately.

Next, an example of a medical connector 100 according to another embodiment of the present invention will be described in detail with reference to FIGS. 13 to 17.

The medical connector 100 according to the present embodiment has the same configuration as that in the above embodiment described with reference to FIGS. 1 to 10, except that a medical device connection portion communication passage 35 has a different configuration, the slit 12 of the valve body 3 is located at a different position, and the positioning projection 31 or the positioning recessed portion 32 are not provided between the outer housing 4 and the inner housing 5.

Figure 13:
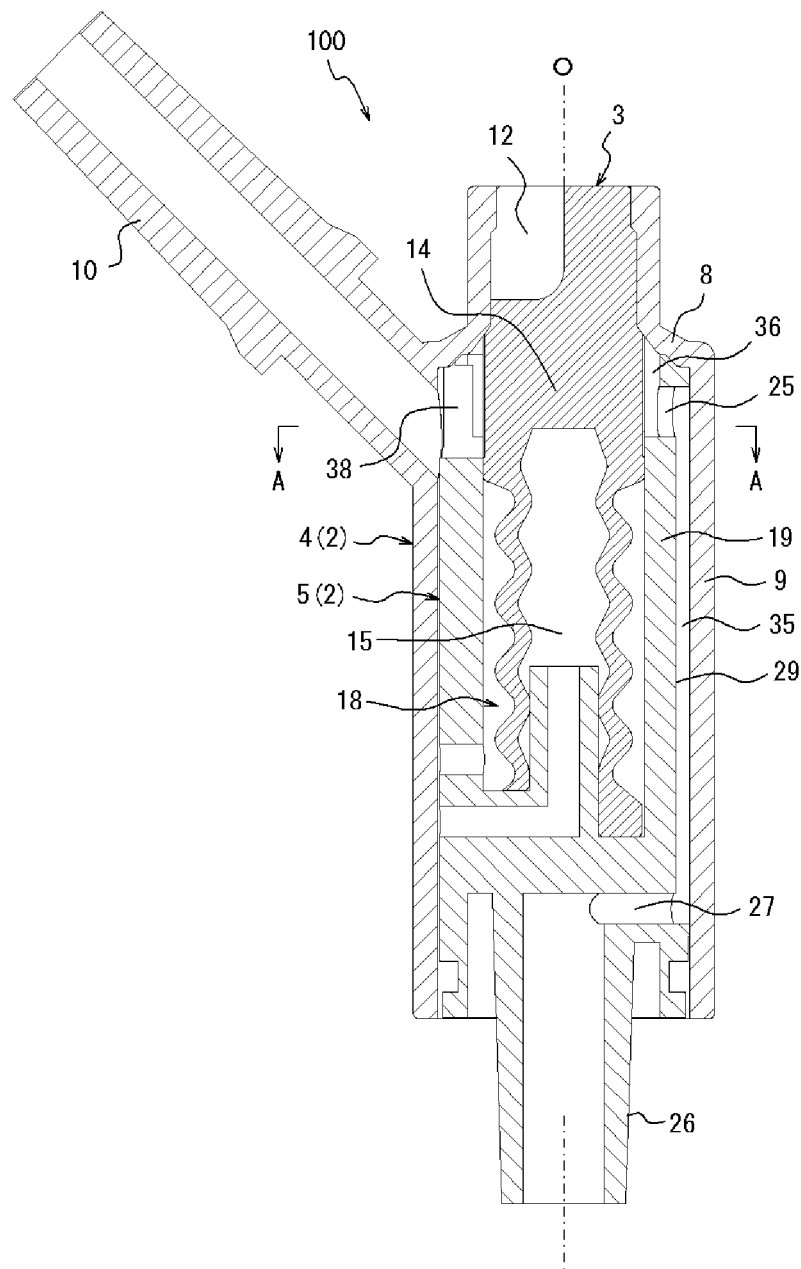
FIG. 13 is a vertical cross-sectional view of a medical connector according to another embodiment of the present invention, where a male connector is not inserted.
Figure 14:
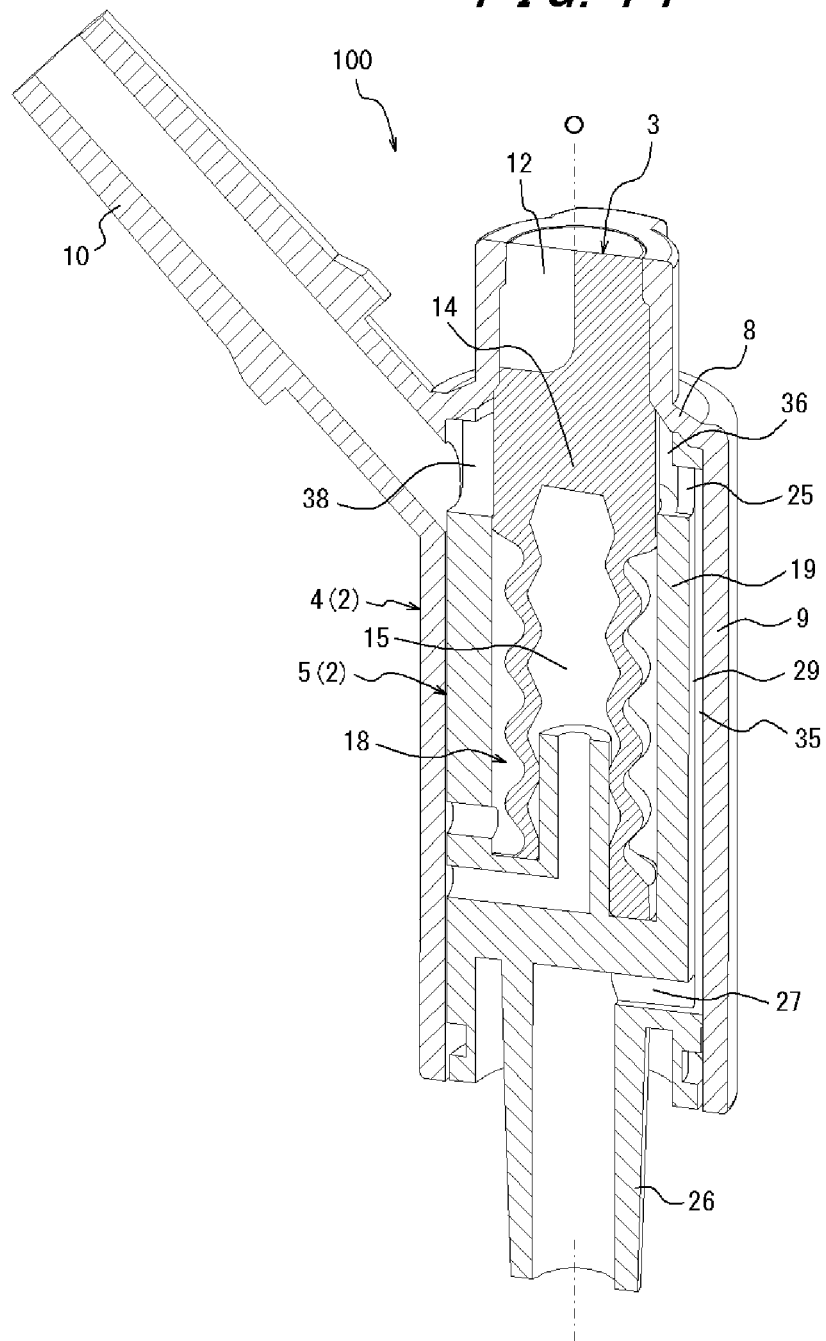
FIG. 14 is a perspective vertical cross-sectional view of the medical connector illustrated in FIG. 13.
Figure 15:
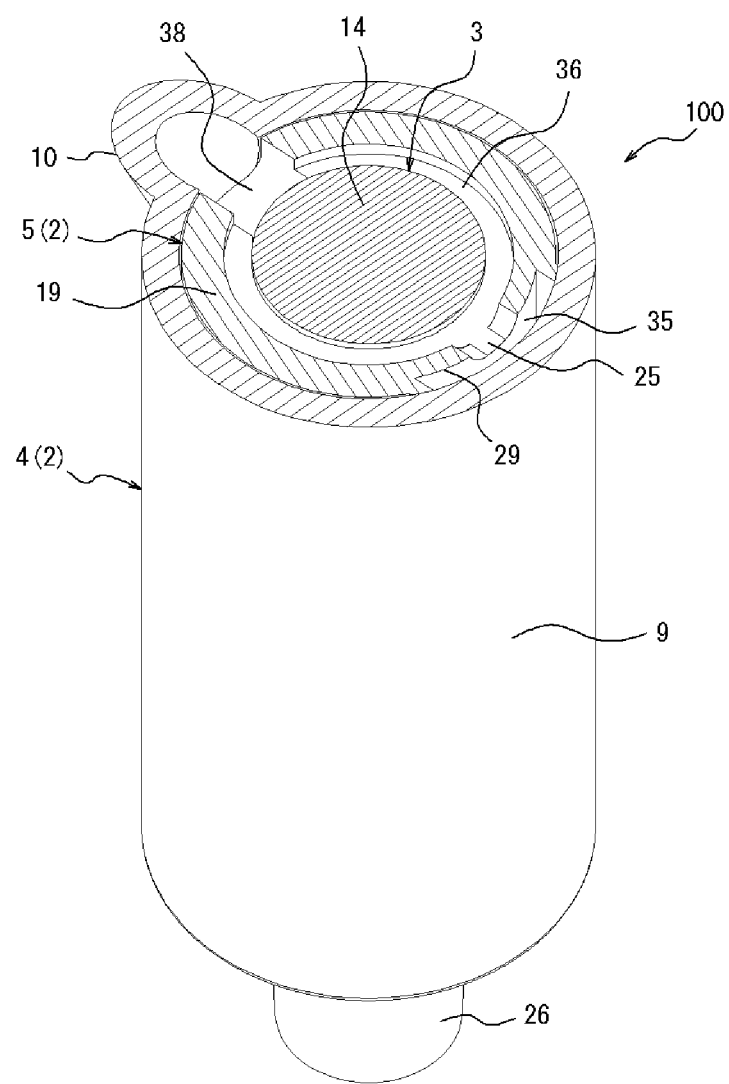
FIG. 15 is a perspective horizontal cross-sectional view illustrating a cross-section taken along the line A-A of FIG. 13.
Figure 16:
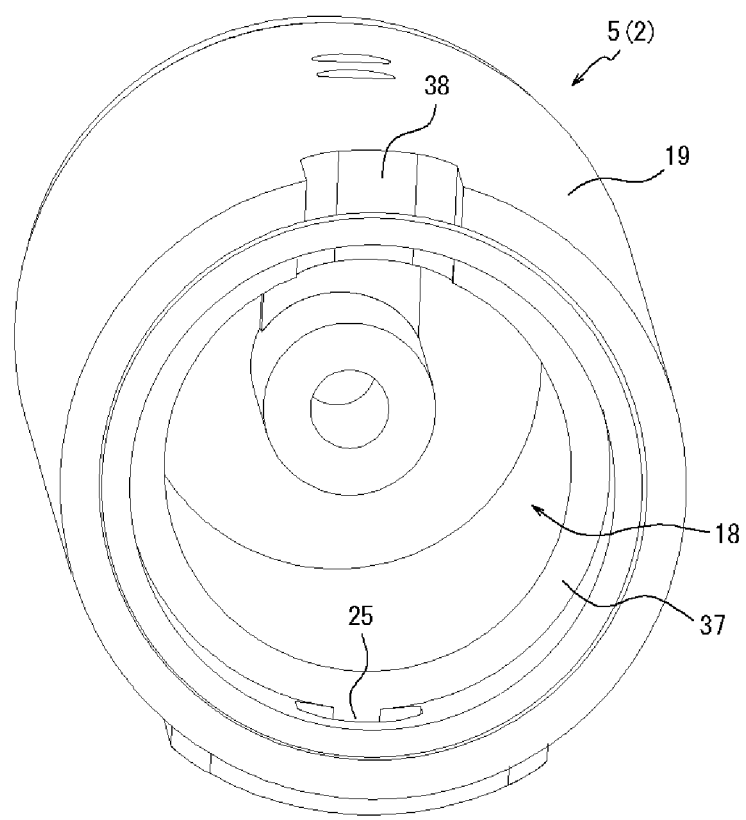
FIG. 16 is a perspective view of an inner housing of the medical connector illustrated in FIG. 13.

That is, as illustrated in FIGS. 13 to 15, in the medical connector 100 according to the present embodiment, the medical device connection portion communication passage 35 includes an annular flow passage 36 surrounding an outer peripheral surface of the body portion 14 of the valve body 3. In the present example, the annular flow passage 36 is defined by a cutout portion 37 formed in an upper inner peripheral surface of the inner peripheral wall portion 19 of the inner housing 5 to have an annular shape (see FIG. 16), the body portion 14 of the valve body 3, and the tapered wall portion 8 of the outer housing 4. Furthermore, the inner peripheral wall portion 19 includes a third through-hole 38 on a side opposite to the first through-hole 25 across the axis O. Therefore, in the present example, the medical device connection portion communication passage 35 is defined by the third through-hole 38, the cutout portion 37, the body portion 14 of the valve body 3, the tapered wall portion 8, the first through-hole 25, the recessed groove portion 29, the outer peripheral wall portion 9, and the second through-hole 27.

Furthermore, in the present example, the slit 12 of the valve body 3 is disposed on a side opposite to the first through-hole 25 across the axis O, that is, near the third through-hole 38. In the present example, the annular flow passage 36 is provided, so that the slit 12 can be disposed, for example, near the first through-hole 25, as illustrated in FIG. 1, or can be disposed at another circumferential position. Alternatively, a plurality of slits 12 can be also disposed. However, the slit 12 is preferably disposed near the third through-hole 38, as described in the present example. Such disposition can guide a fluid flowing from the male connector C to the most upstream portion of the medical device connection portion communication passage 35 while the male connector C is inserted, and the fluid flowing from the male connector C can be inhibited from stagnating in the medical device connection portion communication passage 35.

Figure 17:
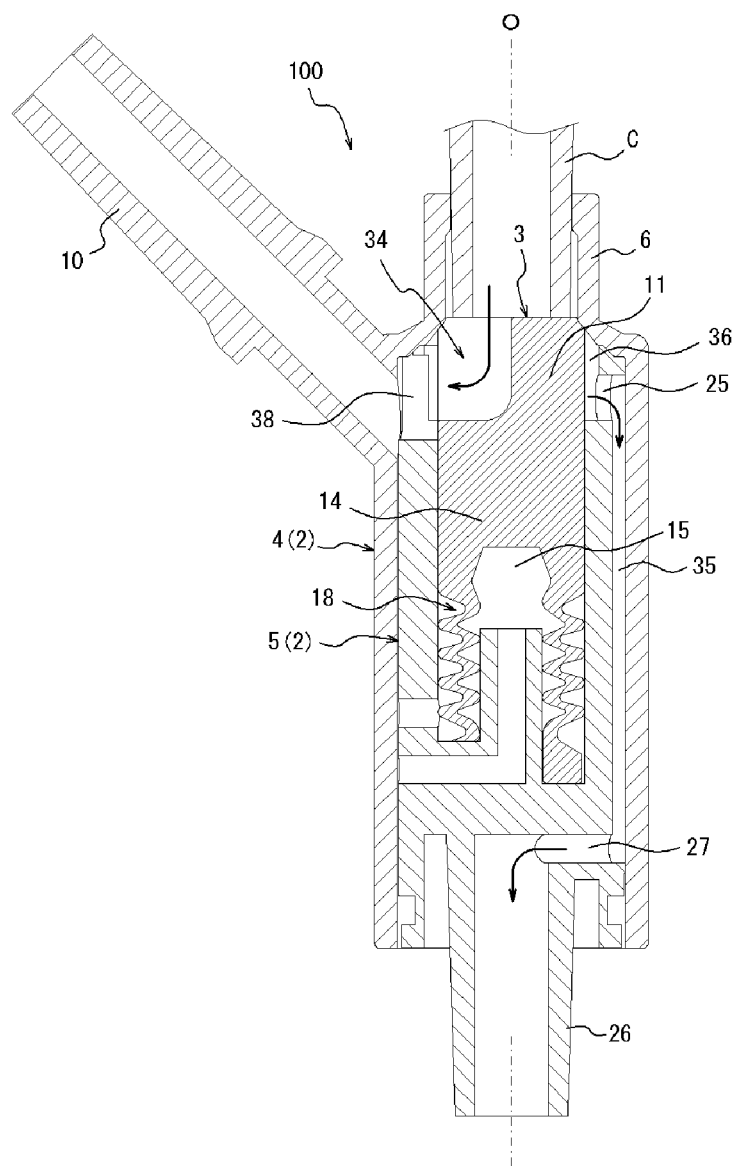
FIG. 17 is a vertical cross-sectional view of the medical connector illustrated in FIG. 13, where a male connector is inserted.

As illustrated in FIG. 17, in the medical connector 100 according to the present embodiment, having such a configuration, the male connector C inserted into the male connector connection portion 6 presses the head portion 11 of the valve body 3 while contracting and deforming the body portion 14 to guide a fluid from the male connector connection portion 6 to the medical device connection portion communication passage 35, through only the gap 34 formed between the head portion 11 and the housing 2. Furthermore, in the medical connector 100, the housing 2 includes the recessed storage portion 18 for storing the body portion 14 of the valve body 3, the valve body 3 is provided with a circumferential sealing portion making sliding contact with the recessed storage portion 18, on the outer peripheral surface of the body portion 14, and the outer peripheral surface of the body portion 14 has a region opposite to the head portion 11 across the sealing portion, and liquid-tightly divided from a fluid flowing in the medical device connection portion communication passage 35.

Therefore, according to the medical connector 100, as in the embodiment described with reference to FIGS. 1 to 10, when the male connector C is removed from the male connector connection portion 6, generation of drawing and extrusion of a fluid are inhibited in the second medical device connection portion 26, and generation of stagnation of the fluid is inhibited in the medical connector 100.

Furthermore, in the present embodiment, as in the embodiment described with reference to FIGS. 1 to 10, the body portion 14 of the valve body 3 forms an inner space (hollow portion 15), and the inner space is liquid-tightly divided from a fluid flowing in the medical device connection portion communication passage 35 upon contraction and deformation of the body portion 14 (see FIG. 17). Therefore, according to the medical connector 100, upon insertion and removal of the male connector C into and from the male connector connection portion 6, contraction and deformation, and expansion and deformation of the body portion 14 of the valve body 3 is facilitated for smooth insertion and removal of the male connector C.

Furthermore, in the present embodiment, as in the embodiment described with reference to FIGS. 1 to 10, while the male connector C is not inserted, a region of at least ½, more preferably at least ⅔, of the outer peripheral surface of the valve body 3 is in contact with the housing 2, or is liquid-tightly divided from a fluid flowing in the medical device connection portion communication passage 35. Therefore, according to the medical connector 100, while the male connector C is not inserted, the valve body 3 can have a surface small enough to be in contact with a fluid flowing in the medical device connection portion communication passage 35, and thus, formation of a stagnation portion of the fluid is inhibited more accurately.

Then, in the present embodiment, the medical device connection portion communication passage 35 includes the annular flow passage 36 surrounding the outer peripheral surface of the body portion 14 of the valve body 3. Therefore, while the male connector C is not inserted, a fluid flowing in the medical device connection portion communication passage 35 flows easily near the outer peripheral surface of the body portion 14 of the valve body 3, and generation of stagnation of the fluid can be further inhibited.

Also in the present embodiment, as in the embodiment described with reference to FIGS. 1 to 10, the medical connector 100 is configured so that the male connector C inserted into the male connector connection portion 6 presses the head portion 11 of the valve body 3 while contracting and deforming the body portion 14 to guide a fluid from the male connector connection portion 6 to the most upstream portion of the medical device connection portion communication passage 35, through only the gap 34 formed between the head portion 11 and the housing 2. Such a configuration can inhibit stagnation of a fluid flowing from the male connector C, in the medical device connection portion communication passage 35, while the male connector C is inserted.

It is to be understood that the above description is only an embodiment of the present invention, and various changes and modifications may be made within the scope of claims.

REFERENCE NUMERAL LIST 1, 1', 100 MEDICAL CONNECTOR
2 HOUSING
3 VALVE BODY
4 OUTER HOUSING
5 INNER HOUSING
6 MALE CONNECTOR CONNECTION PORTION
6a STEPPED PORTION
7 LOCKING PROJECTION
8 TAPERED WALL PORTION
9 OUTER PERIPHERAL WALL PORTION
10 FIRST MEDICAL DEVICE CONNECTION PORTION
11 HEAD PORTION
11a STEPPED PORTION
12 SLIT
13 SHOULDER PORTION
14 BODY PORTION
14a BODY UPPER PORTION
14b BELLOWS PORTION
15 HOLLOW PORTION
16 SEALING PROJECTION
17 RECESSED PORTION
18 RECESSED STORAGE PORTION
19 INNER PERIPHERAL WALL PORTION
20 BOTTOM WALL PORTION
21 INSERTION PROJECTION
22 PROJECTING PORTION
23 FIRST AIR PASSAGE
24 SECOND AIR PASSAGE
25 FIRST THROUGH-HOLE
26 SECOND MEDICAL DEVICE CONNECTION PORTION
27 SECOND THROUGH-HOLE
29 SEALING PROJECTION
29 RECESSED GROOVE PORTION
30 SEALING PROJECTION
31 POSITIONING PROJECTION
32 POSITIONING RECESSED PORTION
33 MEDICAL DEVICE CONNECTION PORTION COMMUNICATION PASSAGE
34 GAP
35 MEDICAL DEVICE CONNECTION PORTION COMMUNICATION PASSAGE
36 ANNULAR FLOW PASSAGE
37 CUTOUT PORTION
38 THIRD THROUGH-HOLE
O AXIS
C MALE CONNECTOR

What is claimed is:

1. A medical connector comprising:
a housing comprising a first medical device connection portion, a second medical device connection portion, and a male connector connection portion;
a valve body comprising:
a head portion configured to close the male connector connection portion, the head portion comprising a slit that extends in a radial direction from a center axis of the male connector connection portion to an outer peripheral surface of the head portion on a first side of the valve body, and
a body portion extending from the head portion; and
a medical device connection portion communication passage defined by the housing and the valve body and configured to guide a fluid from the first medical device connection portion to the second medical device connection portion, wherein the medical device connection portion communication passage comprises:
an annular flow passage surrounding an outer peripheral surface of the body portion of the valve body, and a longitudinal flow passage extending in a longitudinal direction from the annular flow passage;

wherein the medical connector is configured such that, when a male connector is inserted into the male connector connection portion, the male connector presses the head portion of the valve body while contracting and deforming the body portion of the valve body, and the fluid is flowable from the male connector connection portion to the medical device connection portion communication passage through a gap defined by the housing and the slit of the head portion that has been opened by the pressing of the head portion, wherein, in a cross section perpendicular to the center axis of the male connector connection portion, the first medical device connection portion is on the first side of the valve body, the annular flow passage extends around the valve body from the first side of the valve body to a second side of the valve body opposite the first side, and the longitudinal flow passage is entirely on the second side of the valve body, and wherein the medical connector is configured such that all fluid that flows from the first medical device connection portion to the second medical device connection portion does so by passing through the annular flow passage and the longitudinal flow passage that is located entirely on the second side of the valve body.

2. The medical connector according to claim 1, wherein:
while the male connector is not inserted, a region of at least ½ of an overall outer peripheral surface of the valve body is in contact with the housing.

3. The medical connector according to claim 1, wherein the first medical device connection portion projects obliquely with respect to the valve body.

4. The medical connector according to claim 1, wherein:
in the radial direction, the slit extends only from the center axis of the male connector connection portion to the outer peripheral surface of the head portion on the first side of the valve body.

5. The medical connector according to claim 4, wherein:
the first medical device connection portion comprises an opening adjacent to the valve body, and
the cross section perpendicular to the center axis of the male connector connection portion intersects the opening of the first medical device connection portion.

6. The medical connector according to claim 5, wherein:
the opening of the first medical device connection portion is adjacent to the slit of the head portion when the male connector is inserted into the male connector connection portion.

7. The medical connector according to claim 1, further comprising:
a recessed storage portion; wherein:
the body portion of the valve body is located in the recessed storage portion, and
a first space is located between an inner peripheral surface of the recessed storage portion and a first part of the outer peripheral surface of the body portion of the valve body, and wherein an air passage connects the first space to a location outside the medical connector so as to allow air to pass out of the first space when the body portion of the valve body is contracted and deformed.

8. The medical connector according to claim 7, wherein:
the body portion defines a second space therein, and when the body portion is contracted and deformed, the second space is divided in a liquid-tight manner from the fluid flowing in the medical device connection portion communication passage.

9. The medical connector according to claim 8, wherein:
the valve body comprises a circumferential sealing portion at a second part of the outer peripheral surface of the body portion, the sealing portion being configured to make sliding contact with the inner peripheral surface of the recessed storage portion, and
the first part of the outer peripheral surface of the body portion is located opposite to the head portion across the sealing portion and is divided in a liquid-tight manner from the fluid flowing in the medical device connection portion communication passage.

10. The medical connector according to claim 9, wherein:
while the male connector is not inserted, a region of at least ½ of an overall outer peripheral surface of the valve body is in contact with the housing.

11. The medical connector according to claim 9, wherein:
while the male connector is not inserted, a region of at least ½ of an overall outer peripheral surface of the valve body is divided in a liquid-tight manner from the fluid flowing in the medical device connection portion communication passage.

12. The medical connector according to claim 8, wherein:
while the male connector is not inserted, a region of at least ½ of an overall outer peripheral surface of the valve body is in contact with the housing.

13. The medical connector according to claim 1, wherein:
the first medical device connection portion comprises an opening adjacent to the valve body, and
the cross section perpendicular to the center axis of the male connector connection portion intersects the opening of the first medical device connection portion.

14. The medical connector according to claim 13, wherein:
the opening of the first medical device connection portion is adjacent to the slit of the head portion when the male connector is inserted into the male connector connection portion.

15. A method of using a medical connector, the method comprising:
providing a medical connector comprising:
a housing comprising a first medical device connection portion, a second medical device connection portion, and a male connector connection portion,
a valve body comprising:
a head portion configured to close the male connector connection portion, the head portion comprising a slit that extends in a radial direction from a center axis of the male connector connection portion to an outer peripheral surface of the head portion on a first side of the valve body, and
a body portion extending from the head portion, and a medical device connection portion communication passage defined by the housing and the valve body and configured to guide a fluid from the first medical device connection portion to the second medical device connection portion, wherein the medical device connection portion communication passage comprises:
an annular flow passage surrounding an outer peripheral surface of the body portion of the valve body, and
a longitudinal flow passage extending in a longitudinal direction from the annular flow passage,
wherein the medical connector is configured such that, when a male connector is inserted into the male connector connection portion, the male connector presses the head portion of the valve body while contracting and deforming the body portion of the valve body, and the fluid is flowable from the male connector connection portion to the medical device connection portion communication passage through a gap defined by the housing and the slit of the head portion that has been opened by the pressing of the head portion, wherein, in a cross section perpendicular to the center axis of the male connector connection portion, the first medical device connection portion is on the first side of the valve body, the annular flow passage extends around the valve body from the first side of the valve body to a second side of the valve body opposite the first side, and the longitudinal flow passage is certainly on the second side of the valve body, and wherein the medical connector is configured such that all fluid that flows from the first medical device connection portion to the second medical device connection portion does so by passing through the annular flow passage and the longitudinal flow passage that is located entirely on the second side of the valve body; and inserting the male connector into the male connector connection portion such that the male connector presses the head portion of the valve body while contracting and deforming the body portion, and the fluid flows from the male connector connection portion to the medical device connection portion communication passage through the gap defined by the housing and the slit of the head portion.

* * * * *

UNITED STATES PATENT AND TRADEMARK OFFICE
CERTIFICATE OF CORRECTION

PATENT NO. : 11,116,957 B2
APPLICATION NO. : 15/717353
DATED : September 14, 2021
INVENTOR(S) : Ueda et al.

It is certified that error appears in the above-identified patent and that said Letters Patent is hereby corrected as shown below:

On the Title Page

Item (73) Assignee:
Please delete:
"TERUMO KABUSHTKT KAISHA"
Please replace with:
TERUMO KABUSHIKI KAISHA Signed and Sealed this
First Day of March, 2022

Drew Hirshfeld
*Performing the Functions and Duties of the
Under Secretary of Commerce for Intellectual Property and
Director of the United States Patent and Trademark Office*